United States Patent
Bradley et al.

(10) Patent No.: US 7,087,774 B2
(45) Date of Patent: Aug. 8, 2006

(54) VOLATILE COPPER(II) COMPLEXES AND REDUCING AGENTS FOR DEPOSITION OF COPPER FILMS BY ATOMIC LAYER DEPOSITION

(75) Inventors: Alexander Zak Bradley, Drexel Hill, PA (US); David Lincoln Thorn, Los Alamos, NM (US); Jeffery Scott Thornpson, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 28 days.

(21) Appl. No.: 11/017,166

(22) Filed: Dec. 20, 2004

(65) Prior Publication Data

US 2005/0158479 A1  Jul. 21, 2005

Related U.S. Application Data

(62) Division of application No. 10/346,874, filed on Jan. 17, 2003, now Pat. No. 6,939,578.

(60) Provisional application No. 60/349,639, filed on Jan. 18, 2002.

(51) Int. Cl.
   *C07F 1/08*   (2006.01)
   *C23C 16/00*  (2006.01)
   *B32B 9/04*   (2006.01)

(52) U.S. Cl. ............... 556/32; 556/110; 546/2; 427/255.28; 428/411.1

(58) Field of Classification Search ............. 556/32, 556/110; 546/2; 427/255.28; 428/411.1
   See application file for complete search history.

(56) References Cited

U.S. PATENT DOCUMENTS

| 3,594,216 | A | 7/1971 | Charles |
| 5,464,666 | A | 11/1995 | Fine et al. |
| 2005/0003075 | A1* | 1/2005 | Bradley et al. ............ 427/96.8 |
| 2005/0227007 | A1* | 10/2005 | Bradley et al. ............ 427/305 |

FOREIGN PATENT DOCUMENTS

| DE | 4202889 A1 | 8/1993 |
| WO | WO 03/044242 | 5/2003 |

OTHER PUBLICATIONS

McGeachin, Synthesis and properties of some β-diketimines derived from acetylacetone, and their metal complexes, Canadian Journal of Chemistry, vol. 46, 1903-1912, 1968.
N. A. Domnin et al., Zh. Organ. Khim, 1965, 1(1), pp. 658, Reactions of β-Dicarbonyl Compounds with Hydrazines.
M. Ritala and M. Leskela in "Atomic Layer Deposition" in Handbook of Thin Film Materials, H. S. Nalwa, Editor, Academic Press, San Diego, 2002, vol. 1, Chapter 2.

* cited by examiner

*Primary Examiner*—Porfirio Nazario-Gonzalez

(57) ABSTRACT

The present invention relates to novel 1,3-diimine copper complexes and the use of 1,3-diimine copper complexes for the deposition of copper on substrates or in or on porous solids in an Atomic Layer Deposition process.

2 Claims, No Drawings

US 7,087,774 B2

VOLATILE COPPER(II) COMPLEXES AND REDUCING AGENTS FOR DEPOSITION OF COPPER FILMS BY ATOMIC LAYER DEPOSITION

CROSS-REFERENCE TO RELATED APPLICATIONS

This is a divisional of U.S. application Ser. No. 10/346,874 filed 17 Jan. 2003, now U.S. Pat. No. 6,939,578, which claims benefit of U.S. Provisional Patent Application No. 60/349,639, filed 18 Jan. 2002, which is incorporated herein by reference.

FIELD OF THE INVENTION

The present invention relates to novel 1,3-diimine copper complexes and the use of 1,3-diimine copper complexes for the deposition of copper on substrates or in or on porous solids in an Atomic Layer Deposition process. This invention also provides a process for making amino-imines and novel amino-imines.

TECHNICAL BACKGROUND

The ALD (Atomic Layer Deposition) process is useful for the creation of thin films, as described by M. Ritala and M. Leskela in "Atomic Layer Deposition" in *Handbook of Thin Film Materials*, H. S. Nalwa, Editor, Academic Press, San Diego, 2001, Volume 1, Chapter 2. Such films, especially metal and metal oxide films, are critical components in the manufacture of electronic circuits and devices.

In an ALD process for depositing copper films, a copper precursor and reducing agent are alternatively introduced into a reaction chamber. After the copper precursor is introduced into the reaction chamber and allowed to adsorb onto a substrate, the excess (unabsorbed) precursor vapor is pumped or purged from the chamber. This is followed by introduction of a reducing agent that reacts with the copper precursor to form copper metal and a free form of the ligand. This cycle can be repeated if needed to achieve the desired film thickness.

This process differs from chemical vapor deposition (CVD) in the decomposition chemistry of the metal complex. In a CVD process, the complex decomposes on contact with the surface to give the desired film. In an ALD process, the complex is not decomposed on contact with the surface. Rather, formation of the film takes place on introduction of a second reagent, which reacts with the deposited metal complex. In the preparation of a copper film from a copper (II) complex, the second reagent is a reducing agent.

To be useful in an ALD process, the copper complex must be volatile enough to be sublimed without thermal decomposition. Typically, trifluoromethyl group-containing ligands have been used to increase the volatility of the copper complexes. However this approach has drawbacks in the preparation of interconnect layers, since halides adversely affect the properties of the interconnect layer.

The ligands used in the ALD processes must also be stable with respect to decomposition and be able to desorb from the complex in a metal-free form. Following reduction of the copper, the ligand is liberated and must be removed from the surface to prevent its incorporation into the metal layer being formed.

U.S. Pat. No. 5,464,666 describes the decomposition of 1,3-diimine copper complexes in the presence of hydrogen to form copper. This patent also describes the use of 1,3-diimine copper complexes in a Chemical Vapor Deposition process for producing copper-aluminum alloys.

DE 4202889 describes the use of 1,3-diimine metal complexes to i deposit coatings, preferably via a Chemical Vapor Deposition process. Decomposition of the metal complexes in a reducing atmosphere, preferably hydrogen, is disclosed.

S. G. McGeachin, *Canadian Journal of Chemistry*, 46, 1903–1912 (1968), describes the synthesis of 1,3-diimines and metal complexes of such ligands.

N. A. Domnin and S. I. Yakimovich, Zh. Organ. Khim, 1965, 1(4), 658, describe the reaction of aliphatic beta-diketones with unsymmetrical N,N-dialkylhydrazines to produce bis(dialkylhydrazones).

SUMMARY OF THE INVENTION

This invention describes a process for forming copper deposits on a substrate comprising:

a. contacting a substrate with a copper complex, (I), to form a deposit of the copper complex on the substrate; and

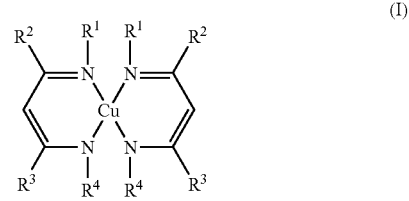

(I)

b. contacting the deposited copper complex with a reducing agent, wherein $R^1$ and $R^4$ are independently selected from the group consisting of H, $C_1$–$C_5$ alkyl, and dimethylamino;

$R^2$ and $R^3$ are independently selected from the group consisting of H, $C_1$–$C_5$ alkyl, phenyl, benzyl, and 4-pyridinyl, with the proviso that the total number of carbons in $R^1$–$R^4$ is 4–12; and the reducing agent is selected from the group consisting of 9-BBN, borane, dihydrobenzofuran, pyrazoline, diethylsilane, dimethylsilane, ethylsilane, methylsilane, phenylsilane and silane.

In another embodiment, this invention provides a 1,3-diimine copper complex, (II),

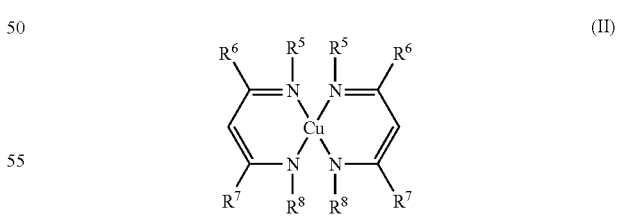

(II)

wherein $R^5$ and $R^8$ are dimethylamino; and $R^6$ and $R^7$ are independently selected from the group consisting of H, $C_1$–$C_5$ alkyl, phenyl, benzyl, and 4-pyridinyl, with the proviso that the total number of carbons in $R^5$–$R^8$ is 4–14; or $R^5$ and $R^8$ are independently selected from the group consisting of H, $C_1$–$C_5$ alkyl, and dimethylamino; and $R^6$ and $R^7$ are selected from the group consisting of H, $C_1$–$C_5$ alkyl, phenyl, benzyl, and 4-pyridinyl, with the proviso that either $R^6$ or $R^7$ is 4-pyridinyl, and the proviso that the total number of carbons in $R^5$—$R^8$ is 4–14.

In another embodiment, this invention provides an article comprising the 1,3-diimine copper complexes, (II), deposited on a substrate.

In another embodiment, this invention provides a process for the synthesis of diimines comprising:

a. contacting an alkylimino-monoketone, (III), with an alkylating agent to form the corresponding O-alkylated derivative, (IV);

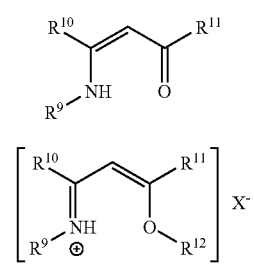

(III)

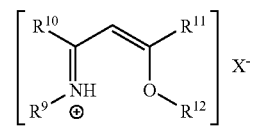

(IV)

b. contacting the O-alkylated derivative, (IV), of step (a) with a primary alkyl amine, $NH_2R^{13}$, to form an immonium salt, (V); and

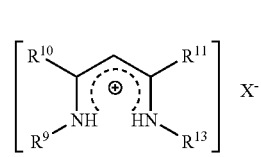

(V)

c. contacting the immonium salt, (V), of step (b) with a strong base to form the corresponding neutral amino-imine (VI):

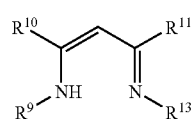

(VI)

wherein $R^{10}$ and $R^{11}$ are independently selected from the group consisting of H, $C_1$–$C_5$ alkyl, phenyl, benzyl, and 4-pyridinyl;

$R^{12}$ is Me or Et;

$R^9$ and $R^{13}$ are independently selected from the group consisting of H and $C_1$–$C_5$ alkyl, with the proviso that the total number of carbons in $R^9$, $R^{10}$, $R^{11}$ and $R^{13}$ is 4–12;

the alkylating agent is selected from the group consisting of dimethyl sulfate, methyl benzenesulfonate, methyltoluenesulfonate, diethyl sulfate, ethylbenzenesulfonate, methyltrifluoromethanesulfonate and ethyl toluenesulfonate; and X is an anion derived from the alkylating agent.

In another embodiment, this invention provides novel amino-imines,

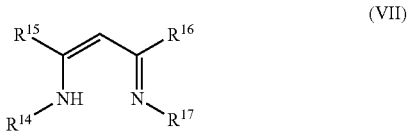

(VII), wherein $R^{14}$ and $R^{17}$ are independently selected from the group consisting of H, $C_1$–$C_5$ alkyl, and dimethylamino; and $R^{15}$ and $R^{16}$ are selected from the group consisting of H, $C_1$–$C_5$ alkyl, phenyl, benzyl, and 4-pyridinyl, with the proviso that either $R^{15}$ or $R^{16}$ is 4-pyridinyl and the proviso that the total number of carbons in $R^{14}$—$R^{17}$ is 4–14.

DETAILED DESCRIPTION

Applicants have discovered an atomic layer deposition (ALD) process suitable for creation of copper films for use as seed layers in the formation of copper interconnects in integrated circuits, or for use in decorative or catalytic applications. This process uses copper(II) complexes that are volatile, thermally stable and derived from ligands which contain only C, H, and N. The ligands are chosen to form copper(II) complexes that are volatile in an appropriate temperature range but do not decompose in this temperature range; rather, the complexes decompose to metal on addition of a suitable reducing agent. The ligands are further chosen so that they will desorb without decomposition upon exposure to a reducing agent. The reduction of these copper complexes to copper metal by readily available reducing agents has been demonstrated to proceed cleanly at moderate temperatures.

In the process of this invention, copper is deposited on a substrate by means of:

a. contacting a substrate with a copper complex, (I), to form a deposit of the copper complex on the substrate; and

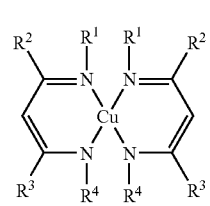

(I)

b. contacting the deposited copper complex with a reducing agent, wherein $R^1$ and $R^4$ are independently selected from the group consisting of H, $C_1$–$C_5$ alkyl, and dimethylamino;

$R^2$ and $R^3$ are independently selected from the group consisting of H, $C_1$–$C_5$ alkyl, phenyl, benzyl, and 4-pyridinyl, with the proviso that the total number of carbons in $R^1$—$R^4$ is 4–12; and the reducing agent is selected from the group consisting of 9-BBN, borane, dihydrobenzofuran, pyrazoline, diethylsilane, dimethylsilane, ethylsilane, phenylsilane and silane.

The deposition process of this invention improves upon the processes described in the art by allowing for lower temperatures and producing more uniform films.

In the copper deposition process of this invention, the copper can be deposited on the surface, or in or on porosity, of the substrate. Suitable substrates include copper, silicon wafers, wafers used in the manufacture of ultra large scale integrated circuit, wafers prepared with dielectric material having a lower dielectric constant than silicon dioxide, and silicon dioxide and low k substrates coated with a barrier layer. Barrier layers to prevent the migration of copper include tantalum, tantalum nitride, titanium, titanium nitride, tantalum silicon nitride, titanium silicon nitride, tantalum carbon nitride, and niobium nitride.

This process can be conducted in solution, i.e., by contacting a solution of the copper complex with the reducing agent. However, it is preferred to expose the substrate to a vapor of the copper complex, and then remove any excess copper complex (i.e., undeposited complex) by vacuum or purging before exposing the deposited complex to a vapor of the reducing agent. After reduction of the copper complex, the free form of the ligand can be removed via vacuum, purging, heating, rinsing with a suitable solvent, or a combination of such steps.

This process can be repeated to build up thicker layers of copper, or to eliminate pin-holes.

The deposition of the copper complex is typically conducted at 0 to 120° C. The reduction of the copper complex is typically carried out at similar temperatures, 0 to 120° C.

Aggressive reducing agents are needed to reduce the copper complex rapidly and completely. Reducing agents must be volatile and not decompose on heating. They must also be of sufficient reducing power to react rapidly on contact with the copper complex deposited on the copper surface. A group of suitable reducing agents have been identified that have not previously been used for copper(II) reduction in an ALD process. One feature of these reagents is the presence of a proton donor. The reagent must be able to transfer at least one electron to reduce the copper ion of the complex and at least one proton to protonate the ligand. The oxidized reducing agent and the protonated ligand must then be easily removed from the surface of the newly formed copper deposit.

Suitable reducing agents for the copper deposition process of this invention include 9-BBN, borane, dihydrobenzofuran, pyrazoline, diethylsilane, dimethylsilane, ethylsilane, phenylsilane and silane. Diethylsilane and silane are preferred.

In a commercial embodiment of the copper deposition process, the copper complexes are added to a reactor under conditions of temperature, time and pressure to attain a suitable fluence of complex to the surface of the substrate. One of skill in the art will appreciate that the selection of these variables will depend on individual chamber and system design and the desired process rate. After deposition on the substrate (e.g., a coated silicon wafer), the complex vapor is pumped or purged from the chamber and the reducing agent is introduced into the chamber at a pressure of approximately 50 to 760 mtorr to reduce the adsorbed copper complex. The substrate is held at a temperature between approximately 0 to 120° C. during reduction. This reaction must be rapid and complete. Reducing agent exposure times may be from less than a second to several minutes. The products from this reaction must then leave the surface. The preferred reagents are the copper 1,3-diimine complex (I, wherein $R^1$, $R^3$, and $R^4$ are Me, and $R^2$ is phenyl) and diethylsilane.

The copper(II) complexes useful in the copper deposition process of this invention fall into two categories: those with symmetrical ligands ($R^1=R^4$ and $R^2=R^3$) and those with unsymmetrical ligands ($R^1 \ne R^4$ and/or $R^2 \ne R^3$). The copper (II) complexes with symmetrical ligands are solids that show good volatility and stability. The preferred ligand from this group is the N,N'-diethyl derivative, in which $R^1=R^4=$Et and $R^2=R^3=$Me. However, the unsymmetrical ligands tend to give more volatile complexes, as indicated by the lower sublimation temperature. For example, the symmetrical N,N'-diethyl derivative can be sublimed at 45 to 50° C. at 100 mTorr pressure, whereas the N-methyl-N'-ethyl derivative ($R^1=$Et and $R^2=R^3=R^4=$Me) sublimes at ca. 25° C. at 100 mTorr. The unsymmetrical complexes can be used at a lower operating temperature than those derived from symmetrical ligands, helping to avoid adverse reactions such as decomposition of the copper complex.

In another embodiment, this invention provides novel 1,3-diimine copper complexes, (II),

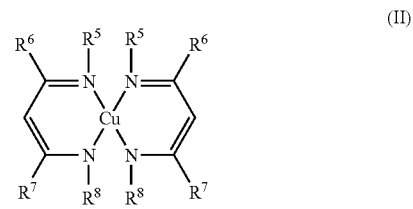

(II)

wherein
$R^5$ and $R^8$ are dimethylamino; and
$R^6$ and $R^7$ are independently selected from the group consisting of H, $C_1$–$C_5$ alkyl, phenyl, benzyl, and 4-pyridinyl, with the proviso that the total number of carbons in $R^5$—$R^8$ is 4–14; or
$R^5$ and $R^8$ are independently selected from the group consisting of H, $C_1$–$C_5$ alkyl, and dimethylamino; and
$R^6$ and $R^7$ are selected from the group consisting of H, $C_1$–$C_5$ alkyl, phenyl, benzyl, and 4-pyridinyl, with the proviso that either $R^6$ or $R^7$ is 4-pyridinyl, and the proviso that the total number of carbons in $R^5$—$R^8$ is 4–14.

The novel copper complexes, (II), are useful in the copper deposition process of this invention. Preferably, $R^5$ and $R^8$ are dimethylamino, and $R^6$ and $R^7$ are $C_1$–$C_5$ alkyl, with the proviso that the total number of carbons in $R^5$—$R^8$ is 5–10.

In another embodiment, this invention provides an article comprising 1,3-diimine copper complexes, (II), deposited on a substrate such as: copper, silicon wafers, wafers used in the manufacture of ultra large scale integrated circuits, wafers prepared with dielectric material having a lower dielectric constant than silicon dioxide, and silicon dioxide and low k substrates coated with a barrier layer. Barrier layers to prevent the migration of copper include tantalum, tantalum nitride, titanium, titanium nitride, tantalum silicon nitride, titanium silicon nitride, tantalum carbon nitride, and niobium nitride.

A new synthetic method for the preparation of amino-imines (precursors to 1,3-diimine ligands) has also been discovered by the Applicants. The literature procedure described by McGeachin requires use of an expensive, unstable alkylating agent (triethyl oxonium tetrafluoroborate). A more practical, commercially scalable process must proceed with high yields and use stable, lower cost reagents. Applicants have found that dimethylsulfate and other inexpensive alkylating reagents can be used in place of the triethyl oxonium tetrafluoroborate salt. These alkylating agents yield the desired amino-imines in high yield, as shown in the examples below. The present process also improves upon the processes described in the art by not requiring a co-solvent, and simplifying the isolation of the desired product.

Applicants' process for the synthesis of amino-imines comprises:

a. contacting an alkylimino-monoketone, (III), with an alkylating agent to form the corresponding O-alkylated derivative, (IV);

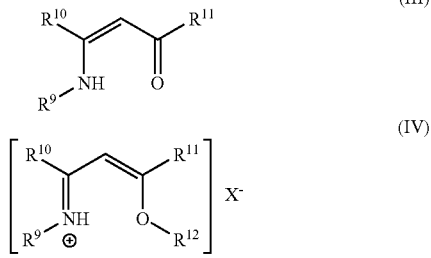

b. contacting the O-alkylated derivative, (IV), of step (a) with a primary alkyl amine, $NH_2R^{13}$, to form an immonium salt, (V); and

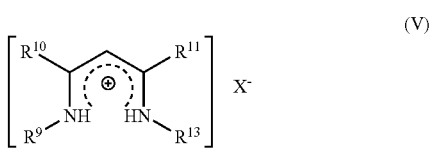

c. contacting the immonium salt, (V), of step (b) with a strong base to form the corresponding neutral amino-imine (VI):

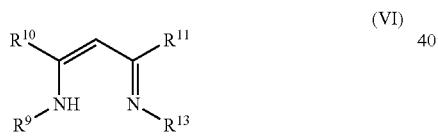

wherein
$R^{10}$ and $R^{11}$ are independently selected from the group consisting of H, $C_1$–$C_5$ alkyl, phenyl, benzyl, and 4-pyridinyl;
$R^{12}$ is Me or Et;
$R^9$ and $R^{13}$ are independently selected from the group consisting of H and $C_1$–$C_5$ alkyl, with the proviso that the total number of carbons in $R^9$, $R^{10}$, $R^{11}$ and $R^{13}$ is 4–12;
the alkylating agent is selected from the group consisting of dimethyl sulfate, methyl benzenesulfonate, methyltoluenesulfonate, diethyl sulfate, ethylbenzenesulfonate, methyltrifluoromethanesulfonate and ethyl toluenesulfonate; and
$X^-$ is an anion derived from the alkylating agent.

In the above process for preparing amino-imines, the alkyl-imino-monoketones, (III), are readily available from the reaction of the β-diketones with amines. The preferred primary alkyl amine, $NH_2R^{13}$, is selected from the group consisting of methylamine, ethylamine, and propylamine. The strong base is selected from the group consisting of sodium methoxide, copper methoxide, and potassium tert-butoxide.

In another embodiment, this invention provides novel amino-imines,

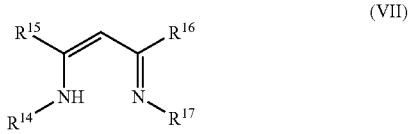

(VII), wherein
$R^{14}$ and $R^{17}$ are independently selected from the group consisting of H, $C_1$–$C_5$ alkyl, and dimethylamino; and
$R^{15}$ and $R^{16}$ are selected from the group consisting of H, $C_1$–$C_5$ alkyl, phenyl, benzyl, and 4-pyridinyl, with the proviso that either $R^{15}$ or $R^{16}$ is 4-pyridinyl, and the proviso that the total number of carbons in $R^{14}$–$R^{17}$ is 4–14.

Preferably, $R^{14}$ and $R^{17}$ are dimethylamino, and $R^{15}$ and $R^{16}$ are $C_1$–$C_4$ alkyl; or $R^{15}$ is 4-pyridinyl and $R^{14}$, $R^{16}$ and $R^{17}$ are $C_1$–$C_4$ alkyl.

The amino-imines, (VII), wherein $R^{14}$ and $R^{17}$ are independently selected from the group consisting of H, $C_1$–$C_5$ alkyl, can be made by the process for making such ligand precursors, as described above. The preparation of amino-imines wherein $R^{14}$ and $R^{17}$ are dimethylamino and $R^{15}$ and $R^{16}$ are methyl is given in Example 7; analogous dimethylamino ligands with other $R^{15}$ and $R^{16}$ substituents can be similarly prepared.

EXAMPLES

All organic reagents are available from Sigma-Aldrich, 940 W. St. Paul Avenue, Milwaukee, Wis., USA). Copper ethoxide was purchased from Alfa Aesar (30 Bond Street, Ward Hill, Mass., USA).

Example 1

Preparation and Reduction of Bis(N-ethyl-4-ethylimino-2-pentene-2-aminato)copper(II)

The 1,3-diimine ligand, $CH_3CH_2N=C(CH_3)-CH_2-C(CH_3)=N-CH_2CH_3 \cdot HBF_4$, was prepared according to a literature procedure (McGeachin). The Cu(II)complex was prepared by reaction of the free base with copper(II) methoxide in methanol. Copper methoxide (0.268 g) was weighed into a 50-mL Erlenmeyer flask. A magnetic stir bar and 5 mL methanol were added. The free ligand was prepared from the tetrafluoroborate salt (1.00 g) by reaction with sodium methoxide; the methoxide solution was prepared by adding NaH (0.105 g) slowly to 5 mL methanol. This methanol solution was added all at once to the rapidly stirred copper methoxide solution along with an additional 5 mL methanol. A purple solution formed immediately. The mixture was stirred for 1 hour at room temperature. Solvent was removed under vacuum. The resulting solid was mixed with hexane; the resulting mixture was filtered through a sintered glass frit with a bed of Celite 545. The cake was washed with hexane until the purple color was no longer visible. The solvent was stripped under vacuum. Sublimation at ca. 100 mTorr pressure and temperature range of 40–115° C. yielded a solid with a melting point of 98–100° C. A sample of this material (ca. 0250 g) was sublimed at 70–80° C. at about 100 mTorr pressure onto a glass cold finger cooled with Dry Ice. A purple film was obtained on the glass surface. After cooling, the kettle containing the copper complex was replaced with one containing diethylsilane. The apparatus was heated under vacuum at 50° C. The purple color of the copper complex faded to white and then to a faint copper color, indicating reduction of the starting copper complex to metal.

Example 2

Preparation of MeC(NHMe)=CHC(=O)Me

Aqueous methylamine (100 g, 40% in water) was added, drop-wise, to, 100 g 2,4-pentanedione. The addition was mildly exothermic; the addition rate was adjusted to keep the temperature between about 35 and 40° C. After the addition was complete, the resulting yellow liquid was stirred 1 hr at room temperature, then subjected to vacuum distillation. The still pot was heated under partial vacuum, such that the first distillation cut (presumably water) came over at 30–35° C. After this fraction was removed, the distillation was discontinued. The contents of the pot solidified upon cooling. By NMR analysis, the title compound was obtained (>95% purity) and in good yield (>90%).

Example 3

Preparation of [MeC(NHMe)=CHC(OMe)Me][MeOSO$_3$]

In the drybox, 4-(methylamino)-3-pentene-2-one (1.00 g) from Example 2 was dissolved in CH$_2$Cl$_2$ (2 mL) and was mixed with dimethylsulfate (1.00 g). The mixture initially formed a yellow solution, cool to the touch, but over the course of an hour, made a thick slurry with some warming. The slurry was filtered and the solids rinsed with CH$_2$Cl$_2$, with an isolated yield of 0.90 g (47%, based on dimethylsulfate). The NMR of the solid product was consistent with title compound.

In the drybox, 4-(methylamino)-3-pentene-2-one (1.08 g) was mixed with CH$_2$Cl$_2$ (0.5 mL) and the slurry combined with dimethylsulfate (1.00 g). The resulting solution was initially cool to the touch but over the course of an hour it solidified, becoming warm to the touch. This mixture was allowed to stand overnight on the stir plate at ambient temperature, then used for the subsequent reaction below. The in situ yield is nearly quantitative based on NMR analysis.

Example 4

Preparation of [MeC(NHMe)=CHC(NHEt)Me][MeOSO$_3$]

The solidified mixture of [MeC(NHMe)=CHC(OMe)Me][MeOSO$_3$], dichloromethane, and unreacted excess MeC(NHMe)=CHC(=O)Me, prepared by the method in Example 9, was treated first with 2 ml THF then with 6 ml ethylamine (2M ethylamine in tetrahydrofuran). The resulting slurry was stirred 15 min at stir plate temperature (about 30° C.), then filtered and dried to yield 1.63 g off-white solids. NMR is consistent with the title composition present as several tautomers, but absolute purity was not established. Crude overall isolated yield for the title composition is 81%, based on dimethylsulfate.

Example 5

Preparation of Bis(N-methyl4-ethylimino-2-pentene-2-aminato)copper(II)

The 1,3-diimine [MeC(NHMe)=CHC(NHEt)Me][MeOSO$_3$], (1.6 g, prepared as described in Example 4) was dissolved in 15 ml methanol. With stirring, potassium t-butoxide (0.71 g) was added. A white precipitate formed immediately and was removed by filtration after stirring 15 min at room temperature. The white precipitate has a $^1$H NMR spectrum [D$_2$O] consistent with K[MeOSO$_3$]. The filtered solution was treated with Cu(OCH$_3$)$_2$ (0.40 g). The resulting purple slurry stirred overnight at room temperature. The solvent was removed, the residue was extracted into hexane, and insoluble material removed by filtration. The hexane was removed by evaporation to leave the title compound as an impure purple paste. The material was purified by sublimation under vacuum (ca. 0.02 torr) at room temperature onto a Dry-Ice-cooled glass surface, or at elevated temperature (ca. 100° C.) onto a room-temperature glass surface.

Example 6

Evaluation of Reducing Agents with Copper(II) 1,3-Diimine Complex

In a dry box, the selected reducing agent (10 equivalents) was added drop-wise (via syringe) to a deep purple solution of the copper complex described in Example 1 (ca. 7–16 mg in 5 mL toluene). The reaction mixture was gradually heated from room temperature to 100° C. If there was no observable change, an additional 10 equivalents of reducing agent were added at 100° C.

a) 9-BBN (0.5M solution in THF). The deep purple solution turned grey/black with heating at 80° C. A black precipitate eventually settled. The black precipitated indicates formation of small copper particles.

b) Borane (1 M solution in THF). The deep purple solution immediately became clear, then tan/brown, followed by gray/green. With slight heating at 45° C., the solution turned black. Eventually, a black precipitate formed.

c) Dihydrobenzofuran. The deep purple solution became darker upon heating at 100° C. An additional 10 equivalent was added and the solution gradually became a dark copper-colored solution with a tan precipitate.

d) Pyrazoline. Upon heating, the deep purple solution gradually turned blue, then green/grey (77° C.), then green/copper color (85° C.), and finally yellow (100° C.). A tan precipitate formed.

e) Diethylsilane. Upon heating (70–80° C.), a black ring formed on the vial followed by a fine copper-colored mirror. A black precipitate was observed.

Example 7

Preparation of Bis(N-dimethylamino-4-dimethylaminoimino-2-pentene-2-aminato)copper(II)

A mixture of 4.0 g pentane-2,4-dione and 6.0 g N,N-dimethylhydrazine was stirred overnight at ambient temperature. The liquid was then vacuum-distilled at a pressure such that the main distillate was collected at 89–90° C. Then 0.92 g of this distillate was mixed with 0.31 g copper(II) methoxide in 5 ml methanol and stirred for 3 days at ambient temperature. The solution was filtered and then evaporated to a purple oil, soluble in hexane and sublimable (ca. 100° C., 0.015 torr).

Example 8

Preparation and Reduction of Bis(N-methyl-4-methylimino-4-phenyl-2-butene-2-aminato)copper(II)

The 1,3-diimine ligand, $CH_3N=C(CH_3)-CH_2-C(C_6H_5)=N-CH_3 \cdot HBF_4$, was prepared according to a literature procedure (McGeachin). The Cu(II) complex was prepared by reaction of the free base with copper(II) ethoxide in tetrahydrofuran; the free base was prepared by reaction of the tetrafluoroborate salt with sodium methoxide (Example 1). Copper ethoxide (0.408 g) was weighed into a 50-mL flask. A magnetic stir bar and ca. 30 mL were added. The free base ligand (1.00 g) in several mL tetrahydrofuran was added all at once to the rapidly stirred copper ethoxide solution. A purple solution formed immediately. The mixture was stirred overnight at room temperature and was then filtered through a sintered glass frit with a bed of Celite 545. The solvent was stripped under vacuum until a dry solid was obtained. Sublimation at ca. 100 mTorr pressure and temperature range of 110–120° C. yielded a solid with a melting point of 98–100° C.

The copper(II) complex (0.018 g) was placed in a vial, which was then placed in a tube. The tube was heated to 165° C. with a nitrogen gas flow (inlet pressure at 5 torr); the exit pressure from the tube was 30 mTorr or less. A second zone in the tube (toward the exit from the tube) was maintained at 100° C. The copper sample sublimed from the initial zone and deposited in the cooler zone, as evidenced by the purple deposit on the walls of the tube. The apparatus was evacuated and then back-filled with diethylsilane. A copper deposit formed on the glass walls in the 100° C. zone, as evidenced by the disappearance of the purple color and the development of a copper-colored deposit.

Example 9

Preparation of N,N'-Diethyl-2,4-pentanediketimine

In the drybox, a 250 mL round bottom flask was charged with 4-(ethylamino)-3-pentene-2-one (30.0 g, 237 mmole) and dimethylsulfate (30.0 g, 238 mmole). The reaction solution was stirred then let stand (12 h) to give a viscous oil. A 2M solution of ethylamine in THF (150 mL) was added with vigorous stirring. The solution was stirred (1 h) until it solidified. The intermediate salt can be isolated (as described by the method in Example 4) or used directly.

A solution of NaOMe (12.8 g, 237 mmole) in MeOH (40 mL) was added to the intermediate salt (vida supra) and let stir (1 h) at ambient temperature. The solvent was removed (in vacuo) to give an oil that was extracted with pentane, filtered and concentrated to give a crude yellow oil. The product, N,N'-diethyl-2,4-pentanediketimine, was isolated by fractional distillation to give a yellow oil (28.6 g) in 72% yield based on the starting 4-(ethylamino)-3-pentene-2-one.

What is claimed is:

1. A 1,3-diimine copper complex, (II),

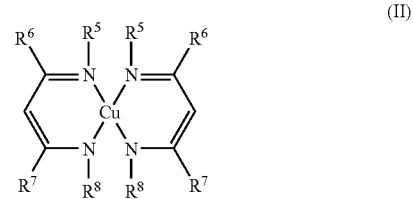

wherein
  $R^5$ and $R^8$ are dimethylamino; and
  $R^6$ and $R^7$ are independently selected from the group consisting of H, $C_1$–$C_5$ alkyl, phenyl, benzyl, and 4-pyridinyl, with the proviso that the total number of carbons in $R^5$–$R^8$ is 4–14; or
  $R^5$ and $R^8$ are independently selected from the group consisting of H, $C_1$–$C_5$ alkyl, and dimethylamino; and
  $R^6$ and $R^7$ are selected from the group consisting of H, $C_1$–$C_5$ alkyl, phenyl, benzyl, and 4-pyridinyl, with the proviso that either $R^6$ or $R^7$ is 4-pyridinyl, and the proviso that the total number of carbons in $R^5$–$R^8$ is 4–14.

2. The 1,3-diimine copper complex of claim 1, wherein $R^5$ and $R^8$ are dimethylamino.

* * * * *